(12) United States Patent
Rosenberg et al.

(10) Patent No.: US 6,695,861 B1
(45) Date of Patent: Feb. 24, 2004

(54) SUTURELESS RETENTION DEVICE

(75) Inventors: Michael S. Rosenberg, Eagan, MN (US); Timothy J. Claude, Coon Rapids, MN (US)

(73) Assignee: InterRad Medical, Inc., Bloomington, MN (US)

( * ) Notice: Subject to any disclaimer, the term of this patent is extended or adjusted under 35 U.S.C. 154(b) by 0 days.

(21) Appl. No.: 10/383,903

(22) Filed: Mar. 7, 2003

Related U.S. Application Data

(60) Provisional application No. 60/412,453, filed on Sep. 20, 2002.

(51) Int. Cl.[7] .................................................. A61B 17/32
(52) U.S. Cl. ........................................ 606/185; 604/174
(58) Field of Search ................................. 606/185, 184, 606/1; 604/174, 175, 164, 264, 165

(56) References Cited

U.S. PATENT DOCUMENTS

| | | | | |
|---|---|---|---|---|
| 5,741,234 A | * | 4/1998 | Aboul-Hosn | 604/174 |
| 5,746,720 A | * | 5/1998 | Stouder, Jr. | 604/175 |
| 2002/0068898 A1 | | 6/2002 | McGuckin, Jr. et al. | |
| 2002/0068899 A1 | | 6/2002 | McGuckin, Jr. et al. | |
| 2002/0165489 A1 | | 11/2002 | McGuckin, Jr. et al. | |

* cited by examiner

*Primary Examiner*—Kevin T. Truong
(74) *Attorney, Agent, or Firm*—Richard C. Emery

(57) ABSTRACT

A retention device for anchoring indwelling catheters, sheath introducers or other medical devices beneath the skin of a patient includes an anchoring mechanism loaded into an anchor sleeve that is attached to an inserted medical device; following insertion into a patient, deploying the device causes the tines of the anchoring mechanism to be extended from the device, thus anchoring the device and any attached medical device securely beneath the patient's skin.

28 Claims, 14 Drawing Sheets

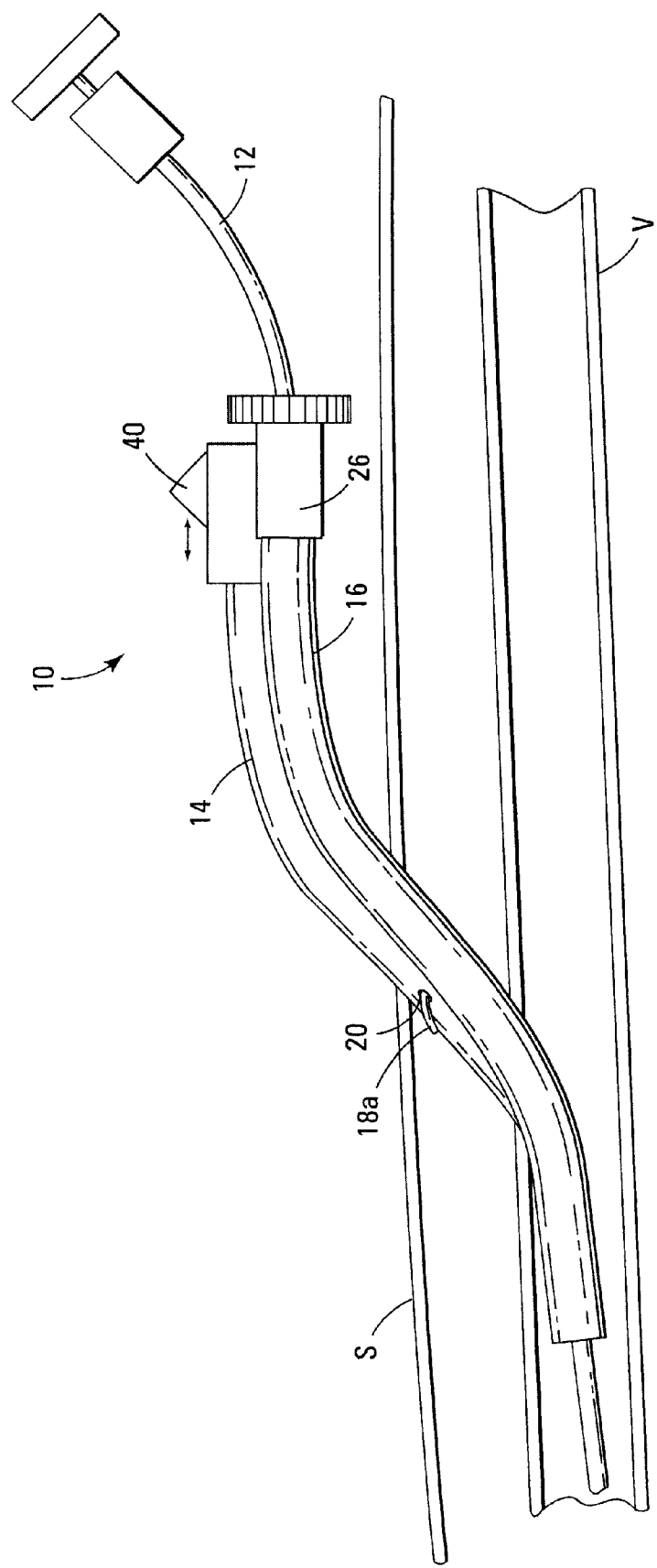

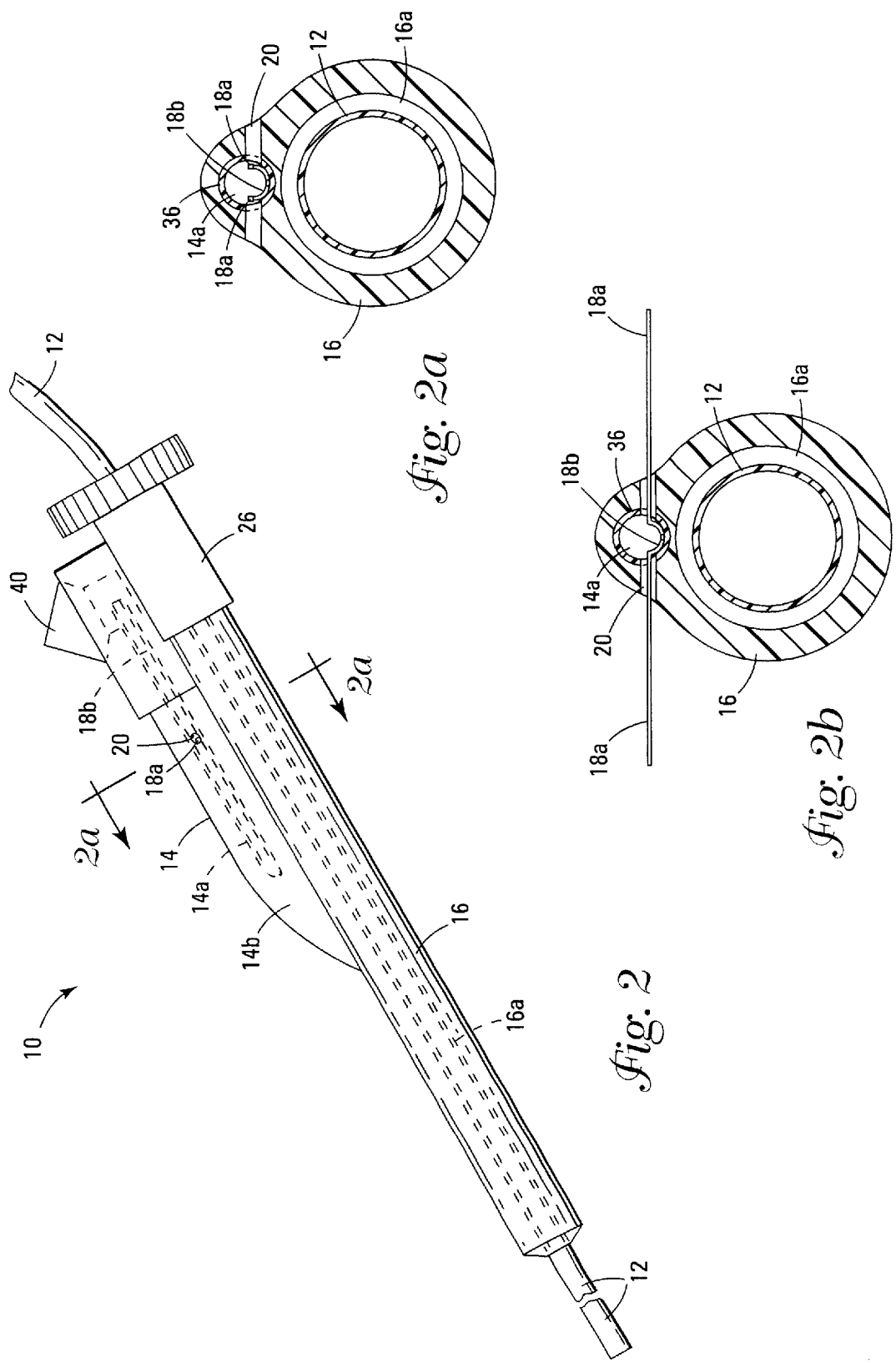

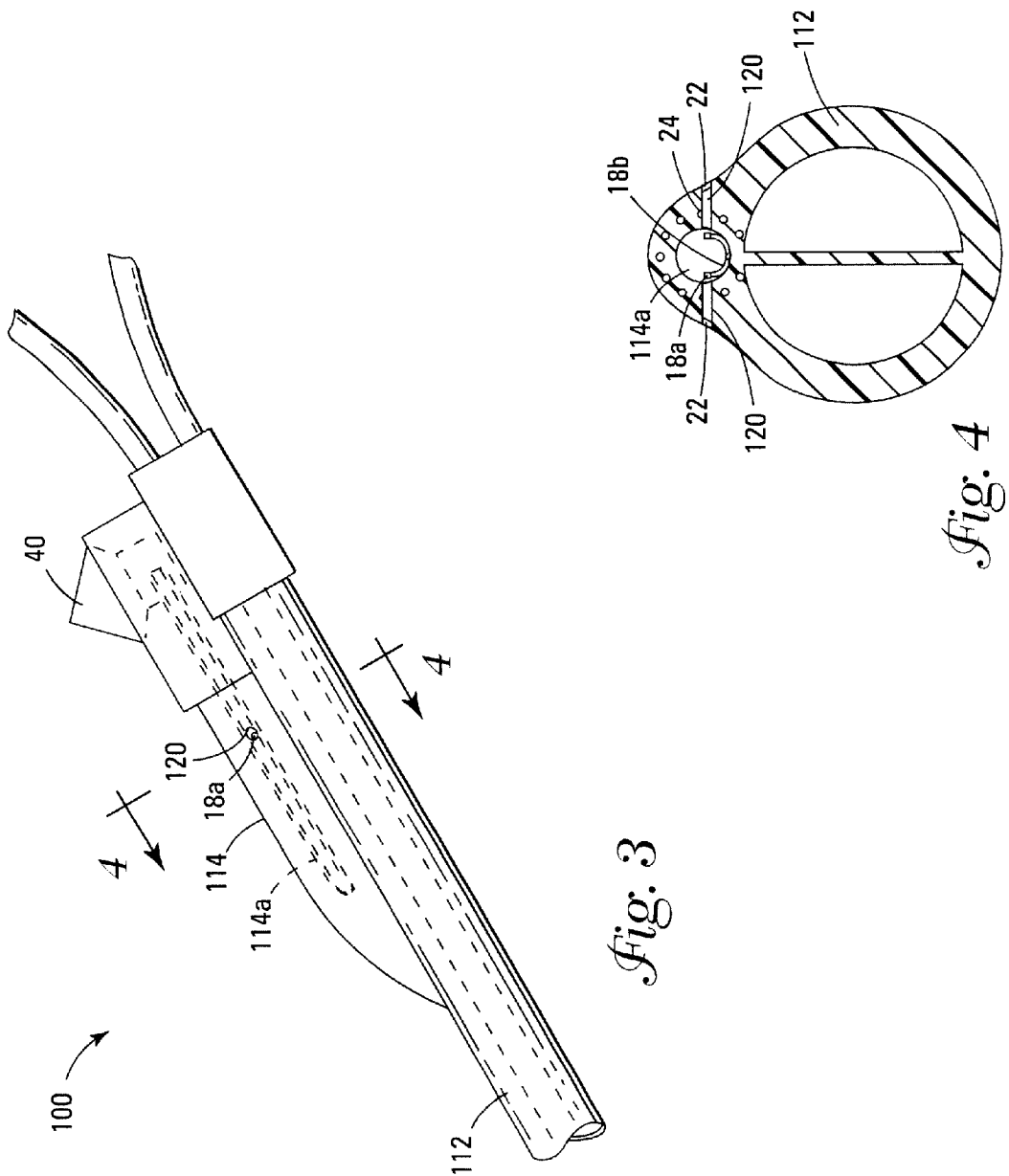

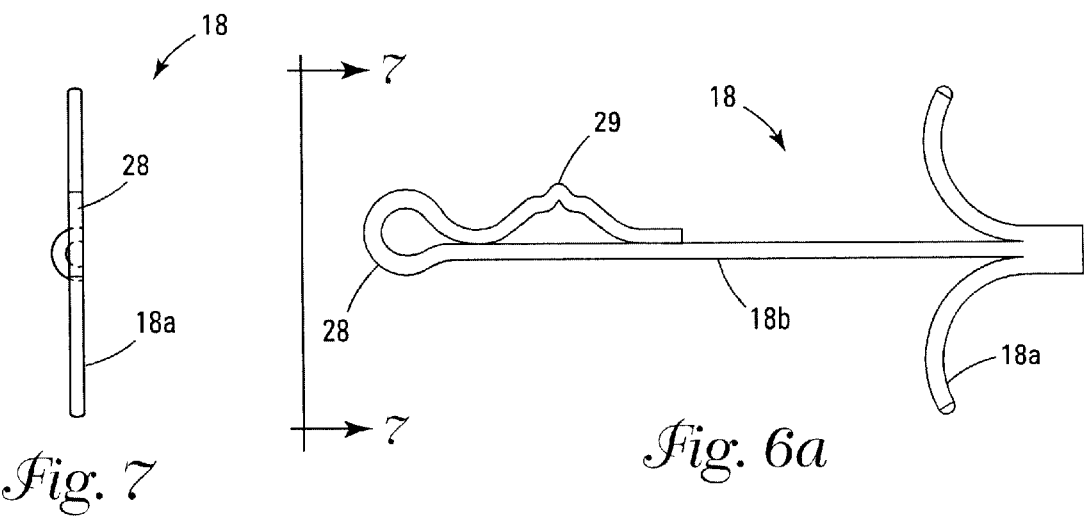
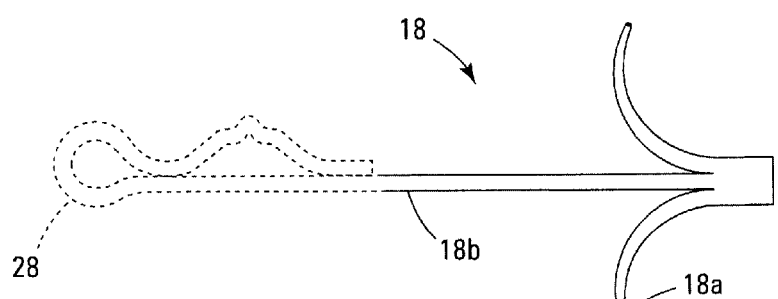

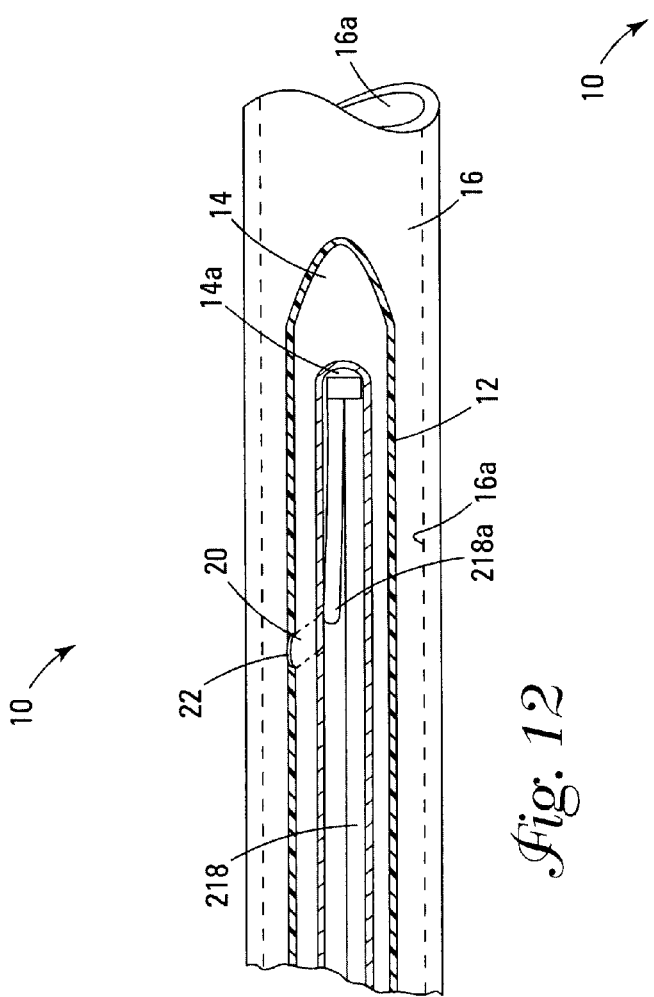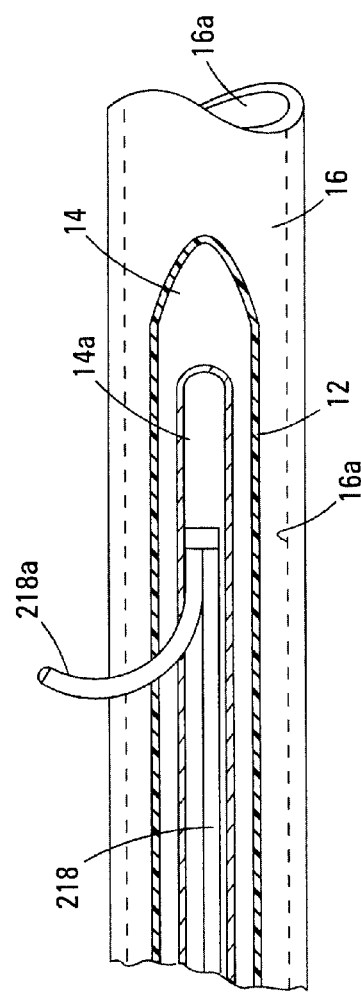

SUTURELESS RETENTION DEVICE

This Application claims the benefit of Provisional Patent Application 60/412,453 filed Sep. 20, 2002, which is herein incorporated in its entirety.

FIELD OF THE INVENTION

The invention relates to a device for securing in-dwelling catheters, sheath introducers, or other temporary or implantable medical devices to patients.

BACKGROUND

Medical treatments requiring the delivery or drainage of various solutions such as antibiotics, cancer drug therapy, blood draws, abscessed biliary material or urinary tract fluids, rely upon an indwelling catheter or sheath introducer to be inserted into the patient for an extended period of time such as thirty or even sixty or ninety days at a time. A requirement for maintaining the catheter or sheath within a patient for such a period is that the catheter or sheath be secured so as not to move excessively during the treatment.

Typically the physician creates an incision or puncture through the patient's skin with the goal of reaching an artery, vein or other vessel to allow insertion of a catheter to deliver a therapeutic substance to or aspirate body fluids from a specific anatomical site. Currently catheters and sheaths are secured utilizing a tab or eyelet formed in the luer hub or Y-connector through which a suture is taken through the tab and skin. A standard 2-0 suture is most often used for this purpose, which is tied off thus securing the catheter within the patient's body. Suturing a catheter to a patient, however, presents several problems: (1) Suturing a catheter to a patient's body makes it difficult to clean and disinfect the area around the catheter insertion point, resulting in a high rate of infection in the area close to the catheter's insertion; (2) The catheter is subject to being dislodged from the patient following introduction resulting in migration of the catheter during treatment; and (3) A sutured catheter is subject to a disoriented patient ripping the catheter loose and tearing the suture out. This can result in patient injury and often necessitates costly replacement or additional corrective procedures.

An additional disadvantage of suturing a catheter to a patient is pain and discomfort to the patient during the period of catheterization, as a result of a long-term suture extending through the patient's skin. Further, different physicians use different suturing and knotting techniques, resulting in a wide variation of pull strengths required to rip out and dislodge the sutured catheter from the patient's body.

Another securement method utilizes adhesive tape. In this method a layer of tape is placed over a cleaned external site on the patient's body after catheter or sheath insertion has been accomplished. The catheter or sheath is adhered to the skin by adhesive friction. This method is ineffective at reducing the incidence of infection. Further, it does not prevent the inadvertent and often violent removal of the catheter prior to completion of treatment.

What is therefore needed is a retention device for a catheter, sheath introducer, or other medical devices that allows for simple and effective anchoring to the patient's body and also reduces the incidence of infection, migration and dislodgment.

SUMMARY

In one embodiment, the invention comprises a device for subcutaneously anchoring a catheter within a patient. The device has an anchor sleeve having a chamber defining at least a single port. An anchor mechanism is loaded into the chamber and has a control rod movable within the chamber between a first position and a second position. A tine is fixedly attached to the control rod at a first end, and also has a second free end. The second end of the tine is capable of flexibly and repeatedly moving between a restrained position near the control rod and an unrestrained position away from the control rod. The tine has a trained shape when in the unrestrained position and the length of the tine is such that the tine is restrained within the chamber when the control rod is in the first position. The port is sized and located so the free end of the tine is proximate the port when the tine is in the first position. Moving the control rod from the first position to the second position causes the free second end of the tine to exit the chamber through the port to at least partially assume the trained shape.

In another embodiment, the device is attached to an introducer sheath.

In yet another embodiment, the device is attached to a catheter.

BRIEF DESCRIPTION OF THE DRAWINGS

In the drawings, identical reference numerals indicate identical or equivalent structure where:

FIG. 1 is a side view of a first embodiment of the retention device following insertion through a patient's skin.

FIG. 2 is a side view of a first embodiment of the invention with an anchor sleeve and anchor mechanism attached to an introducer sheath capable of receiving and securing a catheter, prior to the tine being deployed.

FIG. 2a is a cross sectional view taken through the lines 2a—2a of the embodiment of the invention shown in FIG. 2, with the anchor mechanism loaded into the anchor sleeve, prior to deployment.

FIG. 2b is a cross sectional view taken through the lines 2a—2a of the embodiment of the invention shown in FIG. 2 with the anchor mechanism loaded into and deployed from the anchor sleeve.

FIG. 3 is a side view of a second embodiment of the invention with the anchor sleeve and anchor mechanism attached to a dual lumen catheter body and hub.

FIG. 4 is a cross sectional view taken between points 4—4 of the apparatus shown in FIG.3.

FIG. 6a is a side view of a first embodiment of the anchor mechanism.

FIG. 6b is a side view of the first embodiment of the anchor mechanism having tapered tines.

FIG. 7 is a proximal end view of the first embodiment of the anchor mechanism shown in FIG. 6a.

FIG. 12 is a partial cut away view of the third embodiment of the anchor mechanism loaded into the first embodiment of the retention device prior to deployment of the tine.

FIG. 13 is a partial cut away view of the third embodiment of the anchor mechanism loaded into the first embodiment of the retention device following deployment of the tine.

DETAILED DESCRIPTION

Definitions

Figure 5:
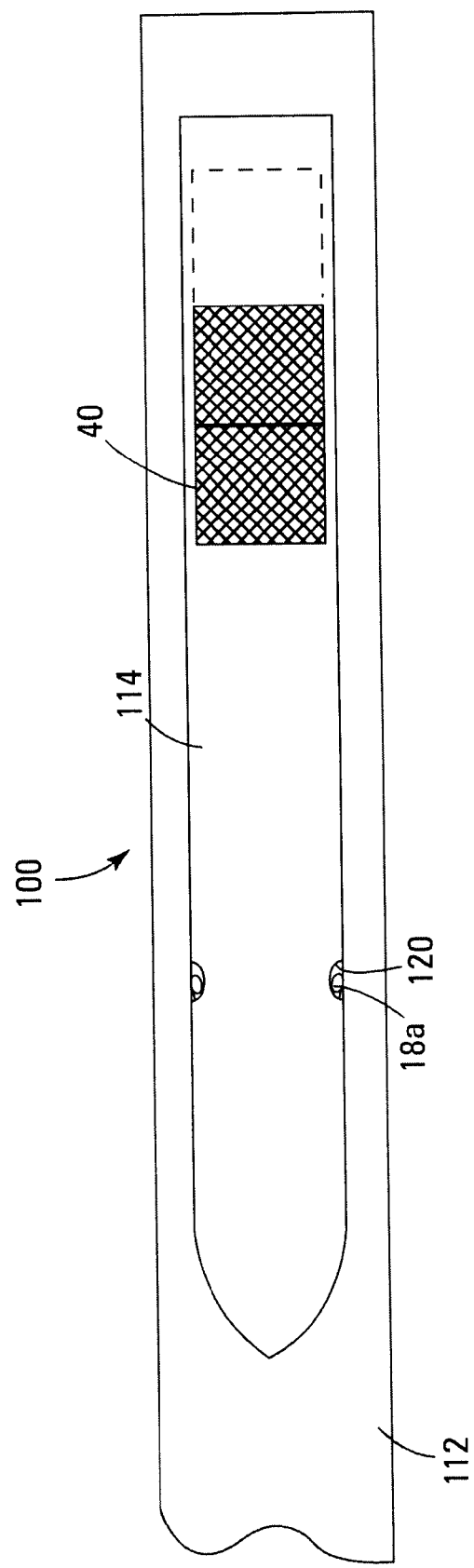
FIG. 5 is a top view of the embodiment of the invention shown in FIG. 3.

"Braid" refers to a structure made of interwoven strands.

"Catheter" is used in its generic sense and refers to any surgical instrument used to deliver a surgical device or chemical substance to a particular location in to the interior of a patient's body.

"Coil" refers to a structure made of a series of rings or spirals.

"Distal" refers to the most distant location from the operator.

"Longitudinal" refers to a lengthwise dimension.

"Port" refers to an opening or a thinning in a wall.

"Proximal" refers to the location closest to the operator.

"Subcutaneous" refers to the space below the skin/dermis.

"Vessel" refers to any anatomical structure that connects organs within a body. Examples include but are not limited to arteries, veins, bile duct, ureter, or other body cavities.

Nomenclature
10 Retention Device (First Embodiment)
12 Catheter
14 Anchor Sleeve
14a Chamber
14b Floor of Anchor Sleeve
16 Introducer Sheath
16a Second Lumen
18 Anchor Mechanism
18a Tine
18b Control Rod
20 Port
22 Membrane
24 Braid
26 Hemostasis Valve
28 Eyelet
29 Lock Spring
32 Recess
34 Key
36 Liner
40 Handle
100 Retention Device (Second Embodiment)
112 Catheter
114 Anchor Sleeve
114a Chamber
118 Anchor Mechanism
118a Tine
118b Control Rod
120 Port
128 Eyelet
129 Lock Spring
130 Weld
218 Anchor mechanism
218a Tine
218b Control Rod
228 Eyelet
229 Lock Spring
230 Weld
400 Retention Device (Third Embodiment)
412 Catheter
414 Anchor Sleeve
414a Chamber
418 Anchor Mechanism
418a Tine
418b Control Rod
420 Port
428 Eyelet
429 Lock Spring
432 Recess
440 Handle
S Skin
V Vessel Construction As shown in FIG. 1, in a first embodiment the present invention comprises a retention device 10 which is useful for securing catheters 12 and other medical devices beneath the skin S of a patient. In the first embodiment, as shown in FIGS. 1 and 2, the invention comprises an anchor sleeve 14 which is integrally attached to an introducer sheath 16 by such means as co-injection molding or co-extrusion. Additional methods of attachment between the anchor sleeve 14 and introducer sheath 16, including but not limited to gluing, ultrasonic welding, mechanical fasteners, heat shrinkable tubing or thermal melting are also contemplated by and therefore within the scope of the invention. As shown in FIGS. 2 and 2a, the anchor sleeve 14 defines a chamber 14a and the introducer sheath 16 defines a lumen 16a. The chamber 14a further defines a floor 14b towards the distal end (unnumbered) of the anchoring sleeve 14 sealably houses the anchor mechanism 18, 118, 218. A sealed chamber 14a is advantageous as it resists and minimizes the flow of blood and other bodily fluids into and out of the retention device 10 during the period of anchoring and catheterization, which could cause infection due to the potentially relatively long period of placement of the retention device 10 within the patient's body. An additional advantage to a sealed chamber 14 is that tissue in-growth is resisted, which could otherwise potentially interfere with and cause seizure of the anchor mechanism 18, 118, 218 thereby making normal removal impossible. A hemostasis valve 26, which is well known in the art, is attached to the proximal end (unnumbered) and collinear with the introducer sheath 16 to prevent the leakage of blood and other bodily fluids from the device 10 during use. The inner diameter of the lumen 16a is sized to be able to accommodate the outer diameter of a catheter 12. Thus, when the device 10 is inserted into a patient, a catheter 12 or other medical device (not shown) will extend first through the hemostasis valve 26, then through the lumen 16a and finally into the desired vessel V, organ (not shown) or body cavity (not shown).

A number of ports 20 in equal number to the number of tines 18a, 118a, 218a are formed through the anchor sleeve 14 to permit deployment of the tines 18a, 118a, 218a during treatment. In a preferred embodiment, a thin membrane 22 of a suitable plastic material such as polyurethane, silicone or latex covers the ports 20. The membrane 22 serves to seal the retention device 10 prior to deployment of the tines 18a, 118a, 218a. As explained in greater detail below, during deployment the tines 18a, 118a, 218a will puncture the membrane 22.

As best shown in FIGS. 3–5, a second embodiment of the retention device 100 comprises an anchoring sleeve 114 integrally attached to a catheter 112 (and associated structures such as a hub/body) by such means as co-injection molding or co-extrusion. The anchoring sleeve 114 further defines a chamber 114a. In additional embodiments the anchoring sleeve 114 can be attached to the catheter 112 by any other suitable means, such as by gluing, ultrasonic welding, mechanical fasteners or thermal melting means. The chamber 114a further defines a floor 114b towards the distal end (unnumbered) of the anchor sleeve 114 and also sealably accommodates the anchor mechanism 18, 118, 218 which, as explained in detail below, extends to form lock spring 29, 129. This resists and minimizes the inflow of blood and other bodily fluids into the retention device 100 during the period of anchoring and catheterization, which could cause infection due to the potentially relatively long period of placement of the retention device 100 within the patient's body. An additional advantage to a sealed chamber is that tissue in-growth is resisted, which could otherwise potentially interfere with and cause seizure of the anchor mechanism 18, 118, 218 thereby making normal removal impossible. In a manner similar to that shown in FIG. 1 with regard to the first embodiment of the retention device 10, the second embodiment of the retention device 100 is likewise introduced (not shown) through a patient's skin S and into a vessel V prior to deployment of the tines 18a, 118a, 218a to secure the retention device 100 to the patient's body.

A number of ports 120 in equal numbers to the numbers of tines 18a, 118a, 218a are formed through a side wall (unnumbered) of the anchor sleeve 114 to permit deployment of the tines 18a, 118a, 218a during treatment. In a preferred embodiment, a thin membrane 22 of a suitable low durometer plastic material such as polyurethane, silicone and latex covers the ports 120. The membrane 22 serves to seal the retention device 10 prior to deployment of the tines 18a, 118a, 218a. As explained in greater detail below, during deployment, the tines 18a, 118a, 218a will puncture the membrane 22.

Suitable materials for the anchor sleeve 14, 114 and introducer sheath 16 include various plastic materials including polyurethane, polyamide, pvax, polyethylene or PTFE reinforced by stainless steel, titanium or nitinol braid 24 or coil (not shown). Carbon fiber materials comprise an alternative braiding material. The reinforcing braid 24 is necessary to add additional strength to constrain the tines 18a, 118a, 218a from premature deployment through the anchor sleeve. In an alternative embodiment, as shown in FIGS. 2a and 2b, the anchor sleeve 14, 114 is reinforced by a liner 36 made of a stronger material such as ultra high density polyethylene, high density polyethylene or nylon and derivatives or combinations of the above. The liner 36 can be a separately molded inserted piece or be incorporated into the anchor sleeve 14, 114 during the molding process. It is also contemplated to insert a liner 36 impregnated (not shown) with a braid 24 or coil (not shown).

The outer surfaces (unnumbered) of the retention device 10, 100 can be coated (not shown) with a variety of commercially available compounds. These include but are not limited to antithrombogenic, antibacterial, or anti-inflammatory compounds to reduce tissue ingrowth, or prevent infection due to the presence of the retention device 10, 100 in the patient for extended periods. These compounds are also useful in improving the biocompatibility of the retention device 10, 100 and include but are not limited to heparin complex solutions, benzalkonium heparinate, triodoecylmethylammonium heparinate, chlorhexidine-silver sulfadiazine, myococycline and rifampin.

Upon introducing a catheter, sheath introducer, or other medical device incorporating the retention device 10 through a patient's skin S and into a vessel V such as an artery (not specifically shown), vein (not specifically shown) or other duct (not specifically shown), vessel or organ (not specifically shown), the tines 18a, 118a, 218a of the anchor mechanism 18, 118, 218 are deployed through the ports 20, 120 thereby securing the catheter 12, 112, introducer sheath 16 or other device (not shown) to the patient's body subcutaneously. The mechanism facilitating tine 18a, 118a, 218a deployment is more fully explained below.

Figure 8:
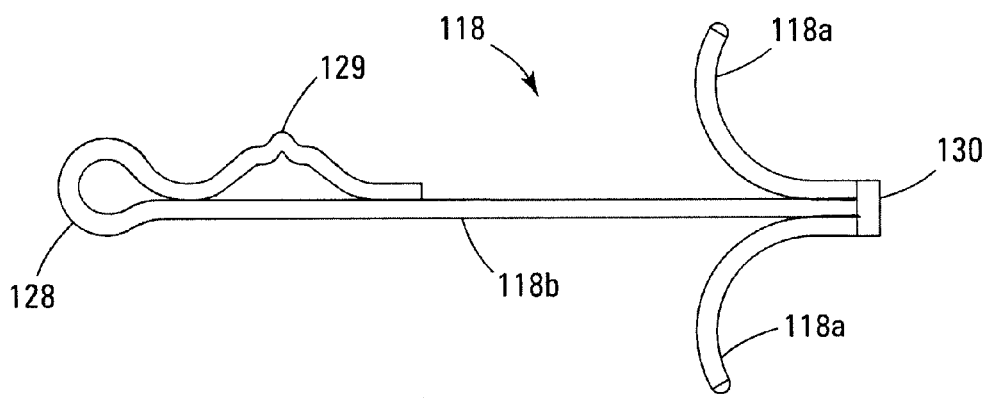
FIG. 8 is a side view of a second embodiment of the anchor mechanism.
Figure 9:
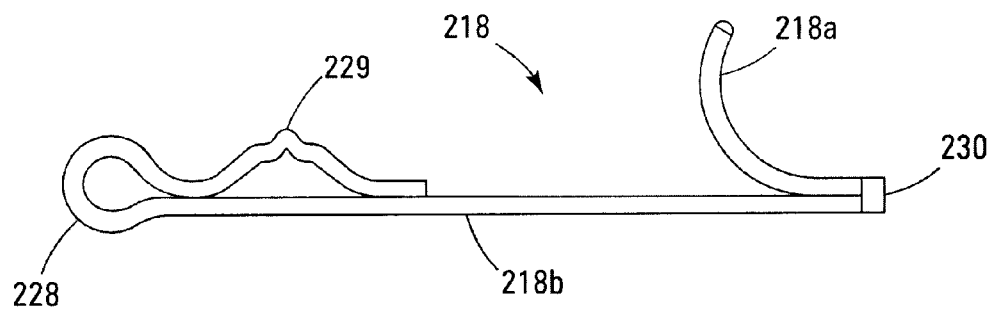
FIG. 9 is a side view of a third embodiment of the anchor mechanism.
Figure 10:
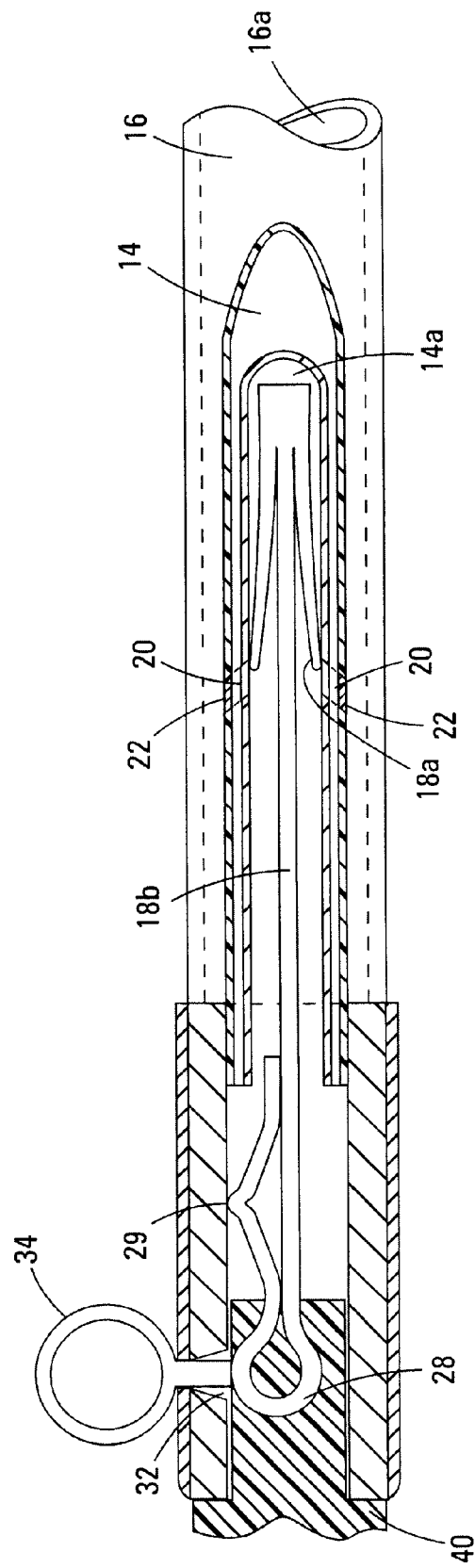
FIG. 10 is a cut away view of the first embodiment showing the lock mechanism prior to deployment of the tines and showing the key inserted into the recess.
Figure 10A:
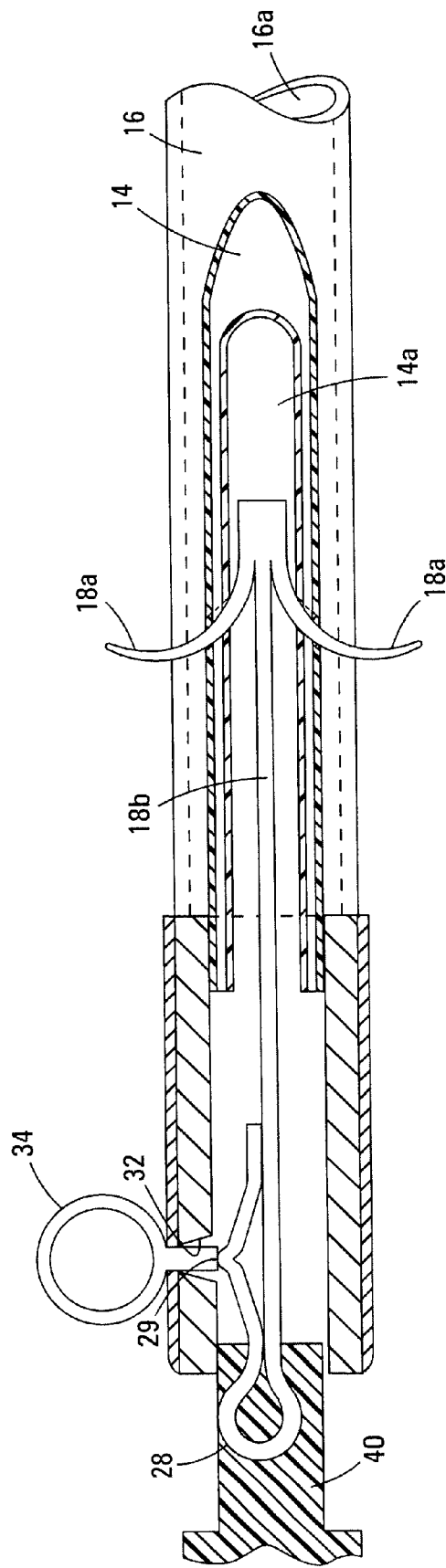
FIG. 10a is a cut away view of the first embodiment showing the lock mechanism following deployment of the tines and the key inserted prior to unlocking the lock mechanism.
Figure 11:
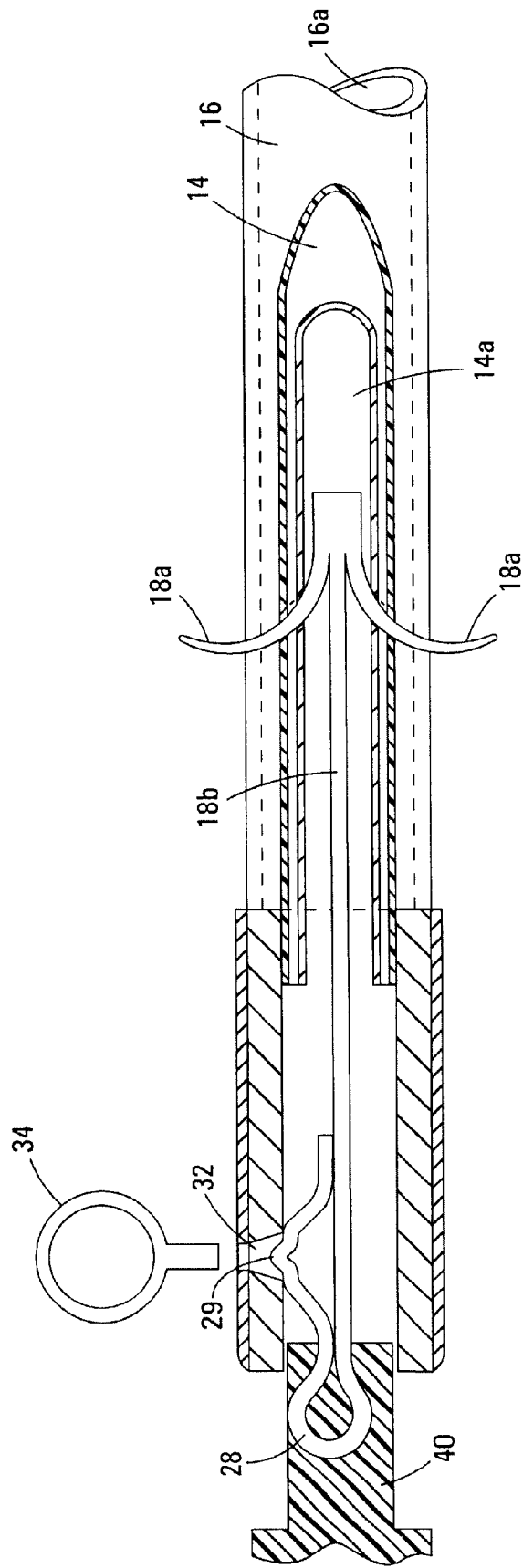
FIG. 11 is a cut away view of the first embodiment of the retention device showing the lock mechanism following deployment of the tines with the key removed from the recess.
Figure 14:
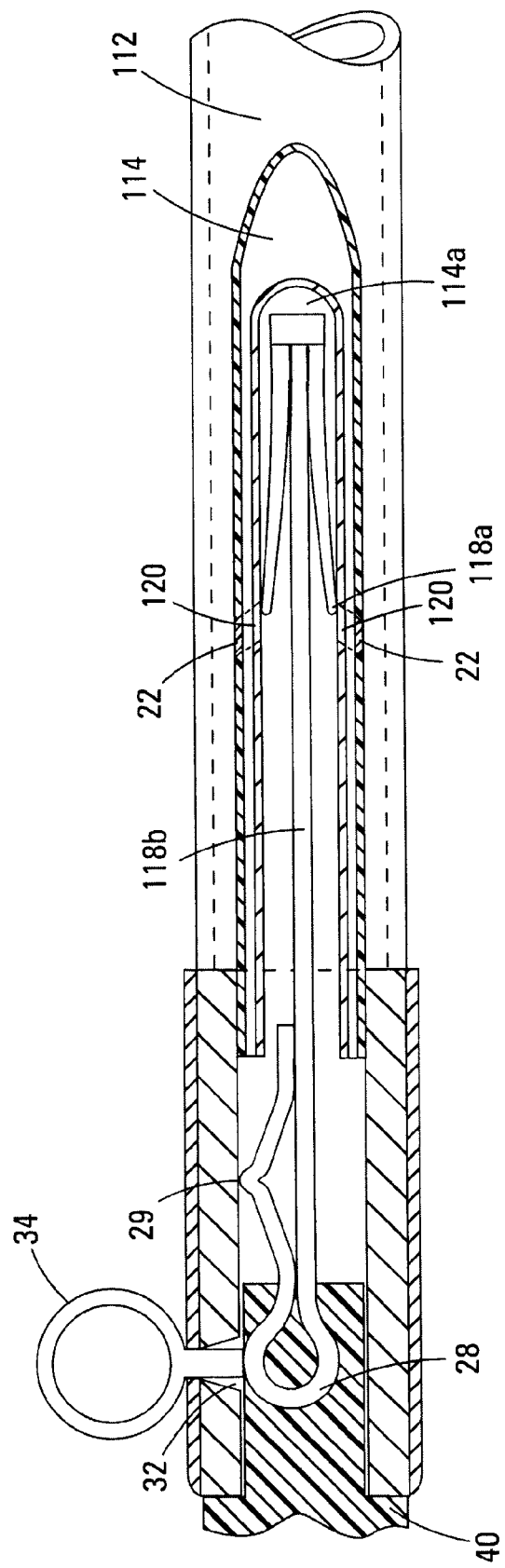
FIG. 14 is a cut away view of the second embodiment of the retention device showing the lock mechanism prior to deployment of the tines.
Figure 15:
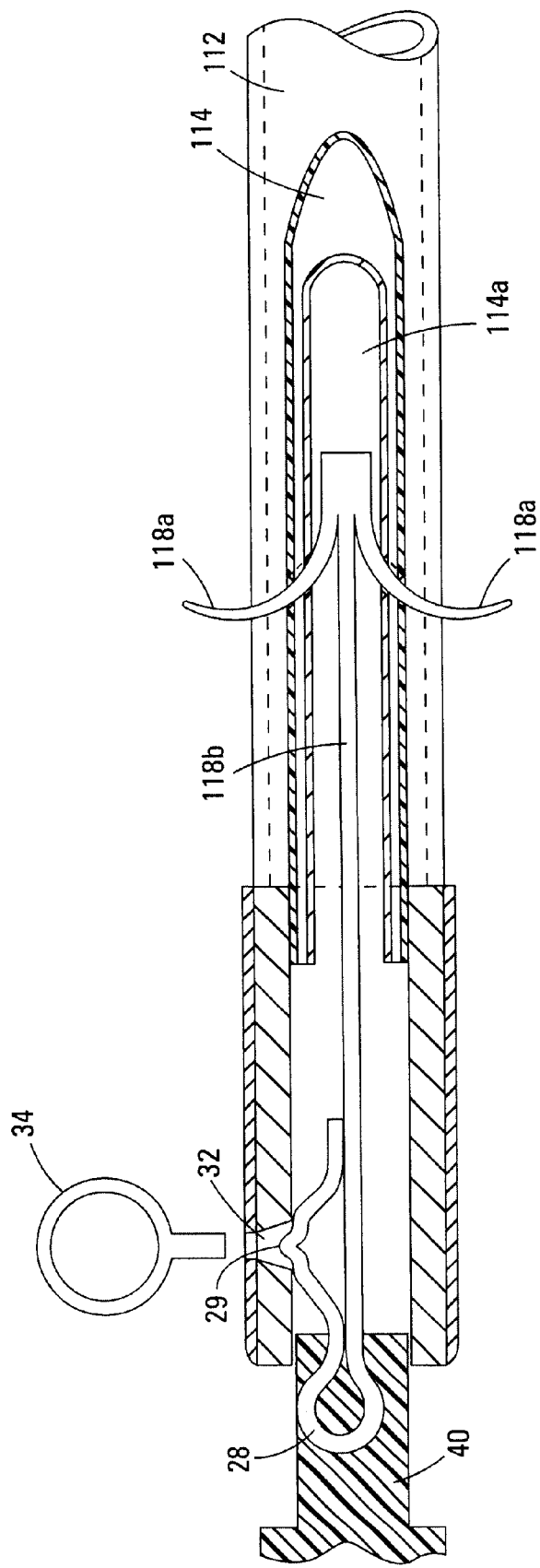
FIG. 15 is a cut away view of the second embodiment of the retention device showing the lock mechanism following deployment of the tines.

A preferred embodiment of an anchor mechanism 18 is best shown in FIGS. 6a, 6b and 7. This embodiment of the anchor mechanism 18 comprises at least a single tine 18a and in a preferred embodiment has two tines 18a but may also have additional numbers of tines 18a such as three (not shown), four (not shown), five (not shown), six (not shown) or even greater numbers of tines 18a (not shown). The tips (unnumbered) of the tines 18a may be sharp (not shown), dull as shown in FIG. 2b or rounded as shown in FIGS. 6a and 8–9. A control rod 18b is integrally attached to the tines 18a. At the proximal end (unnumbered) of the control rod 18b is an eyelet 28 formed integrally with the control rod 18b, which serves either as a convenient grip or as the connector for an attached handle 40. The control rod 18b extends proximally and is trained to bend over to form an eyelet 28. The control rod 18b and eyelet 28 then reverse direction to a distal direction to form the lock spring 29 which is raised above the length of the control rod 18. Together the tines 18a and control rod 18b comprise the anchor mechanism 18. As will be explained in greater detail below, deployment of the tines 18a through the ports 20, 120 in the anchor sleeve 14, 114 secures the retention device 10, 100 within the body of the patient for a period sufficient to complete the desired treatment. Moving the control rod 18b in a proximal direction thus simultaneously moves the fixedly attached tines 18a in a proximal direction, eventually causing the tines 18a to extend through the ports 20, 120 following introduction of the retention device 10, 100 within a patient. As shown in FIG. 6a the tines 18a may have a consistent width or, in an alternative embodiment, as shown in FIG. 6b, the tines 18a may be tapered.

Making the anchor mechanism 18 involves acquiring nitinol tubing having a length sufficient to allow a control rod 18b long enough to extend through the proximal end of the anchor sleeve 14, 114 so as to be able to connect control rod 18b to the handle 40. The tubing preferably has a wall thickness between 0.005 to 0.030 inches, however, lesser and greater wall thicknesses are also contemplated by and therefore within the scope of the invention. Portions of the length of tubing are then cut away by means of well known techniques such as EDM (electron discharge machining), laser cutting, traditional machining or water jet. The remaining portions of the tubing comprise the anchor mechanism 18, and its integrally attached tines 18a, control rod 18b. As explained in detail above, eyelet 28 and lock spring 29 are formed following cutting of the nitinol tubing. Using this manufacturing technique, anchor mechanisms 18 having wide variations are possible. It is also contemplated by the invention to make an integral anchor mechanism 18 from a flat sheet of nitinol. In this embodiment, at least the tines 18a and lock spring 29 are processed so as to have a trained shape when in an unrestrained state somewhere below human body temperature of 37 degrees C. The trained shape of the tines 18a can be a partial arc as shown in FIGS. 2b, 6a, 6b 7, 8, 9, 11, 13 and 15, a semi circular arc (not shown) or even a complete arc (not shown). It should be mentioned that the anchor mechanism could also be made from stainless steel or other alloys such as elgiloy, MP35N, incoloy or other superalloys.

Two alternative embodiments of the anchor mechanism 118, 218 are shown in FIGS. 8 and 9. These anchor mechanisms 118, 218 differ from the anchor mechanism 18 shown in FIGS. 6a, 6b and 7 in that they are constructed from pieces of nitinol ribbon wire comprising tines 118a, 218a and control rod 118b, 218b having welds 130, 230 at a distal end (unnumbered) of the anchor mechanism 118, 218. In a preferred embodiment the welds 130, 230 are accomplished by a laser, however, other welding technologies such as resistance welding and friction welding could also be used. Additionally, hypotubing could used to attach the tines 118a, 218a to the control rod 118b, 218b. The anchor mechanism 118 shown in FIG. 8 has two tines 118a welded to the control rod 118b; the anchor mechanism 218 shown in FIG. 9 has only a single tine 218a welded to the control rod 218b. Control rod 118b, 218b extends proximally and is trained to bend over to form an eyelet 128, 228. The wire forming the control rod 118b, 218b and eyelet 128, 228 then reverse direction to a distal direction to form the lock spring 129, 229 which is raised above the length of the control rod 118b, 218b. Anchor mechanisms 118, 218 function in a similar manner as the anchor mechanism 18 described above. FIG. 12 shows the third embodiment of the anchor mechanism 218 loaded into the first embodiment of the retention device 10 prior to deployment of the tine 218a. FIG. 13 shows the third embodiment of the anchor mechanism 218 loaded into the first embodiment of the retention device 10 following deployment of the tine 218a.

Making the alternative embodiments of the anchor mechanism 118, 218 involves acquiring lengths of nitinol ribbon wire. Separate pieces eventually becoming control rod 118b and tines 118a are then cut to appropriate lengths and attached at a distal end 130, 230 by means of laser welding. In an alternative embodiment, the tines 118a, 218a could also be attached to the control rod 118b, 218b by soldering, gluing or mechanical bonding. It should also be mentioned that anchoring mechanisms 118, 218 could also be similarly made from round wire (not shown) and square wire (not shown). Further, alternative materials such as stainless steel or elgiloy could also be used.

As shown in FIG. 6b, the tines 18a, 118a, 218a, 418a can be tapered toward the free end (unnumbered). The advantage to this configuration is that tapered tines 18a, 118a, 218a, 418a would have increased buckling at the attached end (unnumbered) as well as improved trauma characteristics at the free end (unnumbered).

Following formation of the various embodiments of the anchor mechanism 18, 118, 218, 418 as described above, it is necessary to process at least the tines 18a, 118a, 218a, 418a to have the proper shape upon deployment to anchor the anchoring device within the patient. It is similarly necessary to process the shape of the lock spring 29, 129, 229 to have a shape extending away from the length of the control rod 18b, 118b, 218b, the function of which is explained in detail below. The shape training process also imparts superelasticity, as explained in detail below, to at least the tines 18a, 118a, and 218a, 418a assuming they are made out of nitinol. When the integral anchor mechanism 18, 418 is cut from its source material and when the welded anchor mechanisms 118, 218 are assembled, the tines 18a, 118a, 218a, 418a and lock spring 29, 129, 229 are placed in a forming jig (not shown) which acts as a restraint holding the tines 18a, 118a, 218a, 418a and lock spring 29, 129, 229 in the position they will eventually be trained into. In a preferred embodiment, the tines 18a, 118a, 218a, 418a and lock spring 29, 129, 229 are subjected to a temperature of 500 degrees C. plus or minus 100 degrees C. for less than thirty minutes, depending on the alloy chemistry, dimensions, fixturing and heat source. Different heat sources include salt bath, hot air torch and oven. A heavier and larger fixture will take a longer length of heat treatment time. Following heat treatment, the heated anchor mechanism 18, 118, 218, 418 should be quickly cooled as by an air fan. Making the anchor mechanism 18, 118, 218, 418 from non-superelastic materials such as stainless steel, spring steel or carbon fiber is also contemplated by and therefore within the scope of the invention.

In a preferred embodiment, the anchor mechanism 18, 118, 218, 418 is formed from nitinol wire, sheet or tubing that has been processed to exhibit superelasticity at human body temperature (around 37 degrees C.). The invention also contemplates forming the anchor mechanism 18, 118, 218, 418 from nitinol processed to exhibit thermal shape memory characteristics at human body temperature. Nitinol is an approximate stoichiometric alloy of nickel and titanium; however, other elements such as vanadium are sometimes added in small amounts to alter the mechanical characteristics of the alloy. Chemical composition and processing history primarily determine the particular mechanical properties of a shape memory/superelastic metallic alloy. In general, such an alloy will exist in either one or the other, or combinations of two crystallographic phases. Austenite is the parent crystallographic phase and exists at higher temperatures. Martensite is the other phase and is formed by either subjecting the alloy to lower temperatures or by placing mechanical or physical stress on the alloy while it is in the austenitic phase. Transition temperatures between these two phases can be experimentally determined for a particular alloy. Processing history includes high temperature annealing as well as low temperature forming and deformation. Following standard material and processing specifications, the transitional temperatures that define the alloy's mechanical characteristics are predictable and controllable. Standard transitional temperature designations are given as: $M_s$ for the start of the transition to the martensitic phase, $M_f$ for completion of the transition to martensite, $A_s$ for the start of the transition to the austenitic phase, and $A_f$ for the completed transition to austenite.

Superelasticity is based on phase transition from austenite to martensite. Mechanically induced phase transition from austenite to martensite occurs when the alloy temperature is above $A_f$ and a physical restraint is applied to the alloy. As long as the restraint is in place, the portion of the alloy receiving the stress reverts to the martensitic phase, which remains as long as the stress is maintained. Unless the shape recovery limits are exceeded, when the restraint is removed and the stress is released the alloy returns to its original austenitic phase and shape as long as the temperature is maintained above $A_f$. Thus, when the austenitic, trained shape of the alloy is deformed and held by stress in a new shape, a certain amount of force is exerted by the alloy against the restraint as it resists the new, untrained shape.

The thermal shape memory effect of these alloys has been known much longer than superelasticity. Thermal shape memory occurs as the result of a piece of shape memory alloy metal being deformed while in the lower temperature martensitic phase and then being reheated to a temperature somewhere above $A_s$ which causes the alloy to reform in the austenitic phase. When the crystallographic nature of the alloy is completely austenitic, the alloy's shape returns to the previously trained shape. Shape memory training occurs when a thermal shape memory/superelastic metallic alloy is annealed (heat treated) while restrained in a certain shape. The trained shape will then be maintained unless it is deformed while in the low temperature martensitic phase. Upon reheating the alloy to the austenitic phase, the original shape, which was "learned" in the annealing process, will be "remembered" and returned to. Thus, temperature change is one way of controlling the crystallographic phase of a shape memory/superelastic metallic alloy.

One practical advantage of a shape memory/superelastic alloy over non-superelastic materials is that it can be deformed to a far greater degree without taking a permanent set or kink. In the case of superelastic alloys (i.e., alloys processed to exhibit superelasticity at body temperature), assuming the alloy is above the $A_f$ temperature, removal of the restraint alone is sufficient to resume the original, trained shape. When the alloy is processed to have shape memory characteristics, the martensitic phase alloy need only be subjected to temperatures somewhere above $A_f$ and the alloy will eventually return to its original, trained shape. It is also possible to use a restraint in conjunction with alloys trained to exhibit thermal shape memory characteristics.

Thus, when an anchor mechanism 18, 118, 218, 418 made of nitinol is processed to exhibit superelastic characteristics at human body temperature, it uses superelasticity in two different ways. First, superelasticity (stress-induced martensite) allows the anchor mechanism 18, 118, 218, 418 to be deformed to a degree sufficient to enable it to be loaded into the chamber 14a, 114a, 414a of the anchor sleeve 14, 114, 414 without taking a permanent set or kink. While the anchor mechanism 18, 118, 218, 418 is restrained within the chamber 14a, 114a, 414a assuming the anchor mechanism 18, 118, 218, 418 is maintained at a temperature above $A_f$, the tines 18a, 118a, 218a, 418a contacting the inner walls (unnumbered) of the chamber 14a, 114a, 414a are exerting an amount of force against the chamber 14a, 114a, 414a due to the formation of stress-induced martensite. The force exerted by the tines 18a, 118a, 218a, 418a against the chamber 14a, 114a 414a cause the anchor mechanism 18, 118, 218, 418 to remain in place until the physician determines the retention device 10, 100, 400 is properly introduced into the patient. Following proper introduction, the tines 18a, 118a, 218a, 418a are then deployed through the ports 20, 120, 420 to secure the catheter 12, 112, 412 or sheath introducer (not shown) in place below the skin for the duration of the treatment period. The second way the retention device 10, 100, 400 uses superelasticity is that the processing of nitinol can be varied to program a desired amount of force into the tines 18a, 118a, 218a, 418a. This is advantageous because certain uses of the retention device 10, 100 may require a stronger pull strength than other uses. By programming the superelastic nitinol to a greater or lesser amount of strength, tines 18a, 118a, 218a, 418a can be created that will release at a particular pull strength, rather than be painfully ripped out of the patient.

When the anchor mechanism 18, 118, 218, 418 is formed to exhibit thermal shape memory characteristics at body temperature, the $A_f$ is programmed into the alloy to be somewhere below human body temperature. The $A_s$ of the anchor mechanism 18, 118, 218, 418 is somewhere below room temperature prior to introduction into the patient's body. Alternatively, the anchor mechanism 18, 118, 218, 418 (and consequently the whole retention device 10, 100, 400 into which the anchor mechanism 18, 118, 218, 418 is permanently loaded) can be cooled to a temperature below $M_f$ to place the anchor mechanism 18, 118, 218, 418 in the martensitic phase prior to introduction into the patient's body. When the retention device 10, 100, 400 is being introduced into the body (not shown), means must be used to maintain the temperature of the retention device 10, 100, 400 below $A_s$. Typically, a cold saline drip (not shown) is maintained through the chamber 14a, 114a, 414a during the introduction procedure. Following arrival of the retention device 10, 100, 400 at the treatment site within the patient's body, the tines 18a, 118a, 218a, 418a are advanced from the ports 20, 120, 420 of the anchor sleeve 14, 114, 414, whereupon it is exposed to body temperature, which is above the $A_f$ of the alloy. Exposure to body temperature raises the temperature of the alloy to a point where the tines 18a, 118a, 218a, 418a are in the austenitic phase, returning the tines 18a, 118a, 218a, 418a toward their original, trained shape. Because the tines 18a, 118a, 218a, 418a are deployed beneath the patient's skin S, they may be somewhat restrained by anatomical space limitations and therefore may not fully assume the trained shape.

As shown in FIGS. 10–11 and 14–15, the retention device 10, 100 is provided with a lock mechanism (unnumbered) comprising a lock spring 29 and a recess 32. In the predeployment position, the lock spring 29 is compressed against the inner dimension (unnumbered) of the chamber 14a, 114a. This is due to the normal, trained shape of the lock spring 29 being greater than the inner dimension (unnumbered) of the chamber 14a, 114a. When the control rod 18b, 118b is distally moved by the physician, as discussed above, the tines 18a, 118a, 218a will deploy through the ports 20, 120. Upon reaching a predetermined proximal distance, when the tines 18a, 118a, 218a are fully deployed, the lock spring 29 will reach the internal recess 32 of the chamber 29 and move outward, to fit into the recess 32, thus locking the retention device 10, 100 in the deployed position and securing it in place in the patient. To remove the retention device 10, 100 a key 34 is provided which permits the physician to externally depress the lock spring 29, thus making distal movement of the control rod 18b, 118b possible, allowing eventual removal of the retention device 10, 100 from the patient. It is also contemplated and therefore within the scope of the invention to have a series of recesses (not shown) along the length of the inner dimension of the chamber 14a, 114a allowing the physician a degree of control over the amount of tine 18a, 118a, 218a that is deployed.

Figure 16:
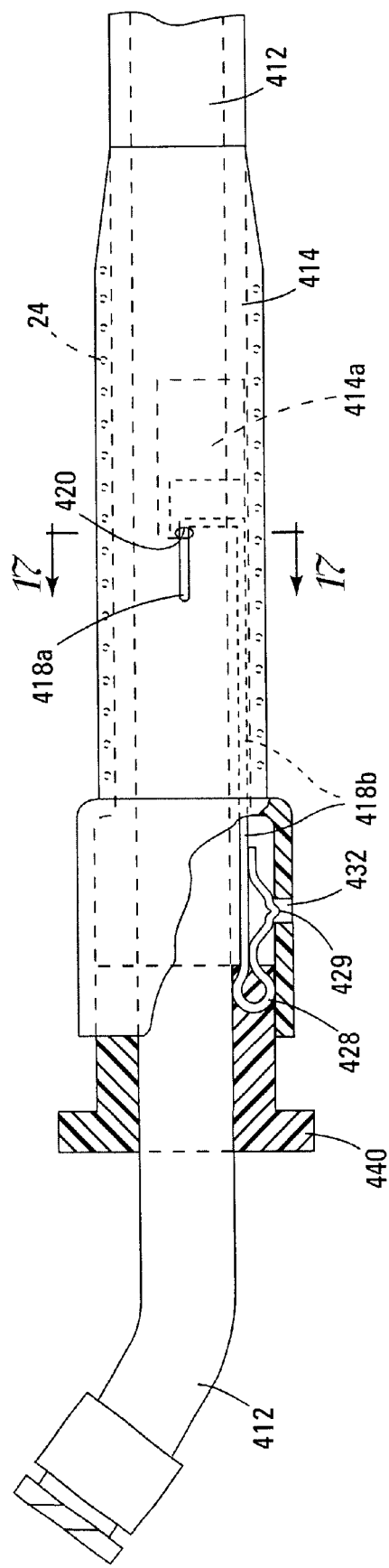
FIG. 16 is a side view of a third embodiment of the retention device showing the anchor mechanism in phantom and the locking mechanism in a cut away view.
Figure 17:
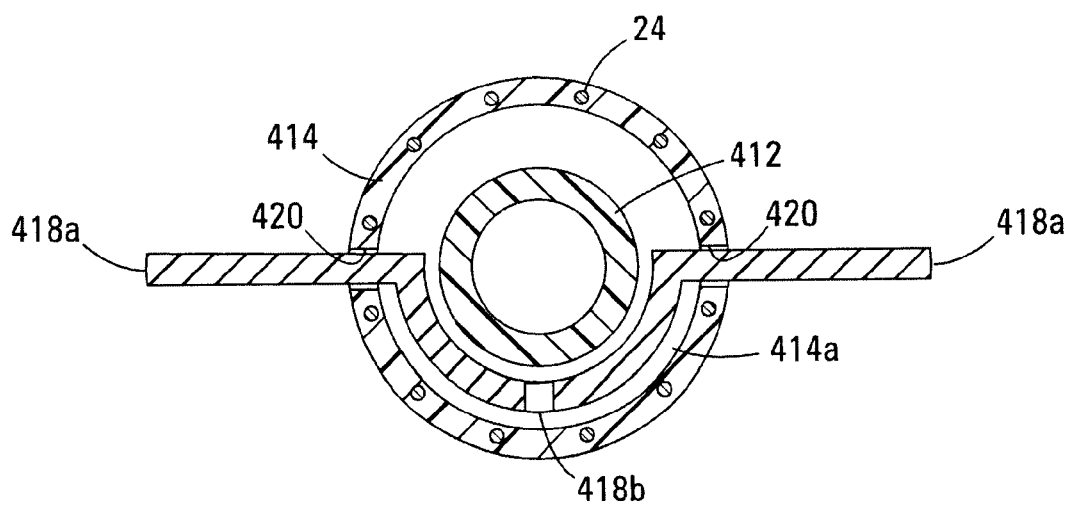
FIG. 17 is a cross sectional view taken through the lines 17—17 of the third embodiment of the retention device.

FIG. 16 shows an additional embodiment of the retention device 400 where the anchor mechanism 418 surrounds the lumen 412 of the catheter 412 to which an anchor sleeve 414 is attached. The anchor sleeve 414 defines a chamber 414a into which the anchor mechanism 418 is loaded prior to deployment. A control rod 418b is distally attached to a plurality of tines 418a. When the control rod 418b is moved proximally the tines 418a will extend through ports 420 that correspond to the individual tines 418a as more fully discussed above. The retention device 400 is fitted with a lock spring 429 which fits into a recess 432 following deployment of the tines 418a. An eyelet 428 is formed at the proximal end (unnumbered) of the control rod 418b. A handle 440 is preferably attached around the eyelet 428 to facilitate deployment of the tines 418a following insertion into the patient. FIG. 17 shows a cross sectional view of the embodiment of the retention device 400 following deployment of the tines 418a.

Use

Using the retention device 10, 100, 400 involves the physician creating an external incision or skin puncture proximate the internal area to be accessed. In most cases it will also be necessary to create an incision by a scalpel or needle in an underlying vessel V to facilitate placement of an indwelling catheter 12, 112, 412. The embodiments of the retention device 10, 400 shown in FIGS. 2–5 and 14–17 have the anchor sleeve 114, 414 directly attached to a catheter 12, 412. The embodiment of the retention device 10 shown in FIGS. 1 and 10–13 show the anchor sleeve 14 attached to an introducer sheath 16. In this embodiment of the retention device 10, following introduction into a patient, a separate catheter 12 is navigated through the lumen 16a of the introducer sheath 16. The catheter 12, 112, 412 when inserted serves as a direct conduit for infusing therapeutic solutions, draining body fluids or delivering mechanical devices to an anatomical site. A needle (not shown) or guidewire (not shown) or dilator/sheath/guiding catheter system (not shown) is used to access the underlying vessel V the interior of which is then entered. The retention device 10, 100, 400 is then adjusted (not shown) to the desired depth but not into the vessel V. Following this, the physician moves the control rod 18b, 118b, 218b, 418b in a proximal direction by grasping and sliding the handle 40 which simultaneously moves tines 18a, 118a 218a, 418a in a proximal direction. The control rod 18b, 118b, 218b, 418b is prevented from excess proximal movement by the length of the tines 18a, 118a, 218a, 418a and locked into the desired position by the lock spring 29 rising into the internal recess 32 in the chamber 14a, 114a, 414a. Moving the control rod 18b, 118b, 218b, 418b proximally thus results in the tines 18a, 118a 218a, 418a puncturing the membranes 22 and thus exiting the anchor sleeve 14, 114, 414 through ports 20, 120, 420. By means of various lock positions available to the physician as a result of the lock system, the tines 18a, 118a 218a, 418a can be extended to the degree desired by the physician. Thus, the tines 18a, 118a 218a, 418a can be extended so as to define a partial arc as shown in FIGS. 1, 2b, 6–9, 11, 13 and 15. Alternatively, if the tines 18a, 118a 218a, 418a have been trained to assume a longer circumference, they can be more fully extended to assume a semi-circular (not shown) or even fully circular (not shown), shape.

Removing the retention device 10, 100, 400 from the patient involves unlocking the lock system by depressing the lock spring 29 from the recess 32 with the key 34 and moving the control rod 18b, 118b, 218b, 418b via the handle 40 in a distal direction. This results in the tines 18a, 118a 218a, 418a simultaneously moving in a distal direction whereby the tines 18a, 118a 218a, 418a reenter the anchor sleeve 14, 114, 414 through the ports 20, 120, 420 whereby the retention device 10, 100, 400 is removed from the patient following completion of the course of treatment.

What is claimed is:

1. A device for subcutaneously anchoring a catheter within a patient, comprising:
   a. an anchor sleeve having a chamber defining at least a single port;
   b. an anchor mechanism loaded into the chamber, the anchor mechanism having;
      i. a control rod movable within the chamber between a first position and a second position,
      ii. a tine having a first end fixedly attached to the control rod, and a second free end,
         (1) the second end of the tine is capable of flexibly and repeatedly moving between a restrained position near the control rod and an unrestrained position away from the control rod,
         (2) the tine having a trained shape when in the unrestrained position,
         (3) the length of the tine is such that the tine is restrained within the chamber when the control rod is in the first position, and
         (4) the port is sized and located so the free end of the tine is proximate the port when the tine is in the first position;
   whereby moving the control rod from the first position to the second position causes the second end of the tine to exit the chamber through the port to at least partially assume the trained shape.

2. The anchoring device of claim 1 wherein the free end of the tine is rounded.

3. The anchoring device of claim 1 wherein the tine has a constant diameter along its length.

4. The anchoring device of claim 1 wherein the free end is narrower than the attached end.

5. The anchoring device of claim 1 wherein the anchor sleeve is reinforced.

6. The anchoring device of claim 5 wherein the anchor sleeve is reinforced by a braid.

7. The anchoring device of claim 6 wherein the braid is nitinol.

8. The anchoring device of claim 6 wherein the braid is stainless steel.

9. The anchoring device of claim 1 wherein the number of ports is equal to the number of tines.

10. The anchoring device of claim 1 wherein the port is sealed by a material puncturable by the tine when the control rod is moved to the second position.

11. The anchoring device of claim 1 wherein the device is attached to an introducer sheath.

12. The anchoring device of claim 11 wherein the introducer sheath defines a lumen capable of receiving a catheter.

13. The anchoring device of claim 11 wherein at least the tine is made of nitinol.

14. The anchoring device of claim 13 wherein the tine is made of nitinol processed to be superelastic below human body temperature.

15. The anchoring device of claim 11 wherein the tine and control rod are longitudinally movable in the chamber.

16. The anchoring device of claim 11 wherein the tine in the unrestrained position defines an arc in a direction away from the proximal end of the control rod.

17. The anchoring device of claim 11 wherein a plurality of tines is attached to the control rod.

18. The anchoring device of claim 17 wherein the tines are integrally attached to the control rod.

19. The anchoring device of claim 17 wherein the tines are separately attached to the control rod.

20. The anchoring device of claim 1 wherein the device is attached to a catheter.

21. The anchoring device of claim 20 wherein at least the tine is made of nitinol.

22. The anchoring device of claim 21 wherein the tine is made of nitinol that is processed to be superelastic below human body temperature.

23. The anchoring device of claim 21 wherein the tine is made of nitinol that is processed to exhibit thermal shape memory when exposed to human body temperature.

24. The anchoring device of claim 20 wherein the tine and control rod are longitudinally movable in the chamber.

25. The anchoring device of claim 20 wherein the tine in the unrestrained position defines an arc in a direction away from the proximal end of the control rod.

26. The anchoring device of claim 20 wherein a plurality of tines is attached to the control rod.

27. The anchoring device of claim 20 wherein the tines are integrally attached to the control rod.

28. The anchoring device of claim 20 wherein the tines are separately attached to the control rod.

* * * * *